United States Patent
January

(10) Patent No.: US 7,012,082 B2
(45) Date of Patent: Mar. 14, 2006

(54) METHOD OF CORRECTING HERG CHANNEL DYSFUNCTION

(75) Inventor: Craig T. January, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/351,758

(22) Filed: Jan. 27, 2003

(65) Prior Publication Data

US 2003/0158228 A1 Aug. 21, 2003

Related U.S. Application Data

(60) Provisional application No. 60/352,731, filed on Jan. 29, 2002.

(51) Int. Cl.
*A61K 31/445* (2006.01)

(52) U.S. Cl. ...................................... 514/315
(58) Field of Classification Search ................. 514/315
See application file for complete search history.

(56) References Cited

U.S. PATENT DOCUMENTS 5,869,479 A * 2/1999 Kreutner et al.
5,990,147 A * 11/1999 Aslanian

FOREIGN PATENT DOCUMENTS

WO WO 01/46188 A1 * 6/2001

OTHER PUBLICATIONS

Q. Gong, et al., "Role of Glycosylation in Cell Surface Expression and Stability of HERG Potassium Channels," Am. J. Physiol. Heart Cir. Physiol. 283:H77–H84, 2002.
C.T. Janaury, et al., "Long QT Syndrome: Cellular Basis and Arrhythmia Mechanism in LQT2," J. Cardio. Electro. 11(12):1413–1418, 2000.
S. Rajamani, et al., "Pharmacological Rescue of Human K+ Channel Long–GT2 Mutations," Circulation, pp. 2830–2835, 2002.
Z. Zhou, et al., "HERG Channel Dysfunction in Human Long QT Syndrome," J. Biol. Chem. 273(33):21061–21066, 1998.
Z. Zhou, et al., "Correction of Defective Protein Trafficking of Mutant HERG Potassium Channel in Human Long AT Syndrome," J. Biol. Chem. 274(44):31123–31126, 1999.

* cited by examiner

*Primary Examiner*—San-ming Hui
(74) *Attorney, Agent, or Firm*—Quarles & Brady LLP

(57) ABSTRACT

A method of shortening prolonged QT intervals in a patient with a trafficking defective HERG mutation is disclosed. In one embodiment, this method comprises the step of treating the patient with an effective amount of fexofenadine whereby the patient's prolonged QT interval is shortened.

6 Claims, 9 Drawing Sheets

METHOD OF CORRECTING HERG CHANNEL DYSFUNCTION

CROSS-REFERENCE TO RELATED APPLICATION

This application claims priority to U.S. provisional patent application No. 60/352,731 filed Jan. 29, 2002.

STATEMENT REGARDING FEDERALLY SPONSORED RESEARCH OR DEVELOPMENT

This invention was made with United States government support awarded to the following agencies: NIH HL60723. The United States has certain rights in this invention.

BACKGROUND OF THE INVENTION

The long QT syndrome (LQTS) is a disorder associated with delayed cardiac repolarization, prolonged electrocardiographic QT intervals, and the development of ventricular arrhythmias (torsades de pointes) and sudden death. LQTS can be congenital (inherited), and one of the principal causes of congenital LQTS are mutations in the human ether-a-go-go-related gene (HERG) producing chromosome 7-linked congenital LQTS or LQT2. HERG encodes the pore-forming subunit of a voltage-gated potassium channel. HERG channel current has properties similar to the rapidly activating delayed rectifier potassium current ($I_{Kr}$) which plays a key role in cardiac action potential repolarization in the mammalian heart. In addition to congenital LQTS, HERG channels are important targets for blockade by many drugs, and it is well established that drug-induced suppression of HERG current causes action potential prolongation and cardiac arrhythmias. This has led to the withdrawal from the world market of several prescription drugs including terfenadine (Seldane), astemizole (Hismanal), cisapride (Propulsid), as well as restriction in the use of other drugs or their failure during drug development because of potential QT intervalrelated toxicity. Therefore, HERG channels have emerged as a very important cardiac ion channel.

A focus of our laboratory has been the, study of HERG potassium channels and how they are involved in the congenital (inherited) and acquired (drug-induced) LQTS. In these studies we use isolated native mammalian heart cells along with cells derived from human origin (human embryonic kidney 293 or HEK293 cells) that are transfected with HERG cDNA encoding the normal (wild-type, see Zhou, et al., *Biophys. J.* 74:230–241, 1998) gene or encoding mutated genes usually of a known human LQT2 mutation (see Zhou, et al., *J. Biol. Chem.* 273:21061–21066, 1998; Furutani, et al., *Circulation* 99:2290–2294, 1999). Cells are then studied using patch clamp electrophysiological, biochemical and immunohistochemical methods to investigate the molecular mechanisms of HERG channel dysfunction caused by LQT2 mutations, and how wild-type and mutant channels are affected by drugs.

An important step in understanding the mechanisms of HERG channel dysfunction in LQT2 was the recognition that some mutations caused defects in biosynthetic processing of HERG channels with the channel protein retained intracellularly in the endoplasmic reticulum (e.g., the channel protein can not reach the cell surface membrane). Many mutations appear to work by this non-trafficking mechanism. However, some mutations are processed similarly to wild-type HERG protein but do not produce functional channels (e.g., channel protein reaches the cell surface membrane but does not work) and other mutations express HERG current but with altered gating properties (e.g., channel protein reaches the cell surface membrane but functions abnormally). These findings were presented in Zhou, et al (Zhou, et al., supra, 1998) and suggested that the loss of HERG channel function in LQT2 mutations is caused by multiple mechanisms including abnormal channel protein trafficking, the generation of nonfunctional channels, and altered channel gating.

We then attempted to "rescue" non-trafficking LQT2 mutations. It was known for a few human diseases that maintaining cells at low temperature rescued some non-trafficking disease-causing protein mutations. This had been shown in 1992 for some mutations in the CFTR channel in cystic fibrosis. We showed temperature correction of the trafficking defect for the LQT2 mutation N470D (asparagine to aspartate at amino acid position 470, see Zhou, et al., *J. Biol. Chem.* 274:31123, 1999). We had previously suggested this mechanism for the G601S (glycine to serine) LQT2 mutation (Furutani, et al., supra, 1999). When expressed at room temperature in Xenopus oocytes, these mutants generate functional HERG channels and in our HEK293 cells stably transfected with these LQT2 mutant channels, culturing the cells at 27° C. also results in the functional expression of HERG current. In the same cells, culturing at 37° C. results in very little current. Biochemical studies confirmed that the trafficking of the mutant HERG protein was temperature-dependent with the mutant protein retained intracellularly at physiological temperature. Although some LQT2 channels can be shown to have both functional and trafficking abnormalities, under physiological conditions abnormal trafficking appears to be the dominant defect.

In addition to lowering temperature, the trafficking defect for the N470D mutant channel can be rescued by pharmacological approaches (see Zhou, Gong, and January, supra, 1999; January, et al., *J. Cardiovasc. Electrophysiol.* 12:1413–1418, 2000). N470D mutant expressing HEK293 cells were cultured at physiological temperature in the presence of low concentrations of drugs known to block with high affinity HERG channels (the antiarrhythmic E-4031, the antihistamine astemizole, and the GI prokinetic agent cisapride). This resulted in the appearance on western blot analysis of the mature HERG protein band. When the drugs were washed off the cells large amplitude HERG current could be recorded confirming pharmacological rescue. Drugs that do not block HERG channels, such as nifedipine, do not mimic this effect. One interpretation of these findings is that drugs binding with high affinity to HERG channels may act as chemical or pharmacological chaperones to stabilize protein folding or assembly of mutant protein in a conformation that permits trafficking to the plasma membrane.

SUMMARY OF THE INVENTION

In one embodiment, the invention is a method of shortening prolonged QT intervals in a patient with a trafficking defective HERG mutation, wherein the patient has a prolonged QT interval comprising the step of treating the patient with an effective amount of fexofenadine, whereby the patient's prolonged QT interval is shortened. Preferably, the patient has a N47OD or G601S mutation.

In one embodiment, the amount of fexofenadine is between 40–80 mg every 12 hours.

In another embodiment, the amount of fexofenadine is between 100–250 mg daily.

Other embodiments of the invention are described below.

BRIEF DESCRIPTION OF THE SEVERAL VIEWS OF THE DRAWINGS

FIG. 1A shows the voltage clamp protocol and representative current records for control conditions and terfenadine treatment. FIG. 1B shows activation curves for peak tail current amplitude fit with the Boltzmann equation for control conditions ($V_{1/2}$=−30.6±2.3 mV, k=6.4) and after 24 hours of 0.05 μM ($V_{1/2}$=−20.8±9.1 mV, k=4.1) and 1 μM terfenadine treatment for 24 hours followed by drug washout for 1 hour ($V_{1/2}$=−27.2±4.4 mV, k=7.2). FIGS. 1C and D show normalized peak tail current amplitude versus time, and block of the current by application of 1 μM terfenadine (arrows).

FIG. 2B shows activation curves for peak tail current amplitude fit with the Boltzmann equation for control conditions ($V_{1/2}$=−30.6±2.3 mV, k=6.4) and after 24 hours of 0.05 μM ($V_{1/2}$=−33.0±2.2 mV, k=5.1), 0.5 μM ($V_{1/2}$=−33.6±4.8 mV, k=8.4), 1.0 μM ($V_{1/2}$=−30.0+1.2, k=6.3) or 5 μM ($V_{1/2}$=−27.5±2.3, k=8.5) fexofenadine treatment. FIG. 2C shows the concentration-dependence relation for pharmacological rescue by fexofenadine. The Hill equation intersects the Y-axis at the control current value. Number of experiments for each data point is given in parenthesis. FIG. 2D shows the concentration-dependence relations for fexofenadine block of WT (■) and N470D (●) channels obtained by fitting the data points with the Hill equation. Number of experiments for each data point is given in parenthesis.

FIG. 3A shows the voltage clamp protocol and representative current records for control conditions and fexofenadine treatment. FIG. 3B shows activation curves for tail current peak amplitude fit with the Boltzmann equation for control conditions ($V_{1/2}$=−9.5±3.4 mV, k=6.9) and after 0.05 μM ($V_{1/2}$=−16.5±6.4 mV, k=6.9) or 1.0 μM ($V_{1/2}$=−14.0±4.1 mV, k=7.5) fexofenadine treatment.

FIG. 4A shows the voltage clamp protocol, and representative current records for control conditions and fexofenadine treatment. FIG. 4B shows I–V plots for control conditions and after 1 μM fexofenadine treatment, with the current measured at the beginning of the 5.7 second long step to −50 mV.

FIG. 6A shows culture of cells expressing HERG WT channels in fexofenadine (1 μM) for 24 hours had no effect on the 135 and 155 kDa protein bands. FIG. 6B shows the S620T mutation shows 135 and 155 kDa protein bands similar to WT.

FIG. 7A shows the voltage clamp protocol is shown with control current traces. Temperature-dependent rescue at 27° C. and fexofenadine-mediated pharmacological rescue are shown in FIG. 7B and FIG. 7C, respectively. FIG. 7D I–V plots show averaged current data recorded after cell culture at 27 or 37° C. Culture at 27° C. resulted in larger amplitude HERG current (p<0.002 at all voltages >−50 mV). FIG. 7E I–V plots show averaged current data recorded following pharmacological rescue for control (no drug), fexofenadine or E-4031. Culture in fexofenadine resulted in larger amplitude HERG current (p<0.002 at all voltages >−50 mV compared to control), whereas, with E-4031 there was no change in HERG current amplitude (p>0.05 at all voltages compared to control).

FIG. 8A is a Western blot analysis of the N470D/S620T double mutant shows a single protein band at 135 kDa, in contrast to WT. The N598Q lane shows a single protein band at 132 kDa. N470D/S620T expressing cells cultured in fexofenadine or E-4031 show only the 135 kDa band. FIG. 8B I–V plots show averaged HERG currents from cells cultured in different fexofenadine concentrations. FIG. 8C shows the concentration-dependence relation for pharmacological rescue (solid line, ▲) are shown along with data previously reported for the N470D mutation (dashed line, ■). FIG. 8D shows the concentration-dependence of HERG current block by fexofenadine is shown for the N470D/S620T double mutation (▲). Drug block was minimal in contrast to previous findings with the N470D mutation (dashed line, ■) or WT channels (dotted line, ●) where high concentration of fexofenadine caused block.

FIG. 9A demonstrates that the N470D/S620T double mutation, E-4031 did not modify temperature-dependent rescue. FIG. 9B shows that fexofenadine produced an additive effect in cells cultured at both 27 and 37° C. (p<0.05 at all voltages >−10 mV comparing ♦ with ●, and p<0.002 at all voltages >−50 mV comparing ▲ with ■).

DESCRIPTION OF THE INVENTION

Figure 1:
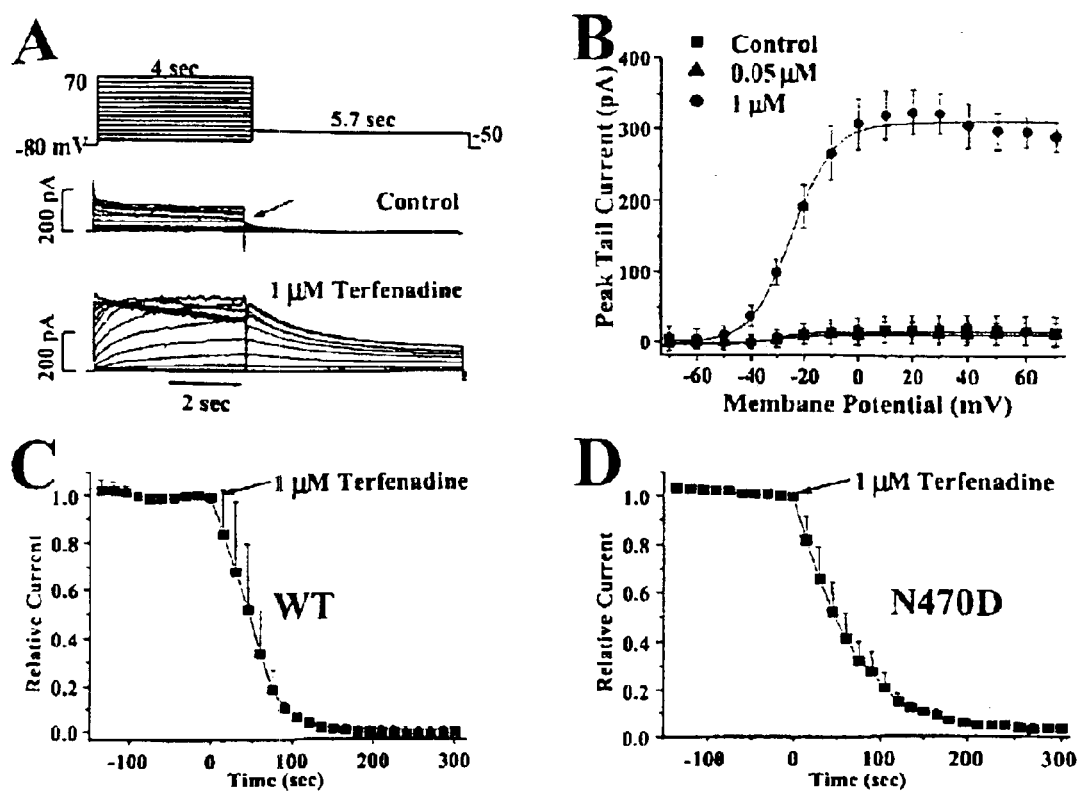
FIG. 1 demonstrates the effect of terfenadine on HERG wild-type (WT) and N470D mutant channels.

Therapy for congenital LQT, including patients with LQT2, has involved the use of beta-adrenergic receptor blocking drugs, the occasional use of cardiac sympathetic denervation, and the implantation of devices to control bradycardia and manage life threatening arrhythmias. Patients are advised to avoid drugs that block potassium channels and aggravate QT interval prolongation, interfere with drug metabolism or lower the serum potassium. More recently, the concept of gene-specific therapy has become attractive in LQT with an example being the use of sodium channel blocking drugs to reduce the late current in LQT3. For LQT2, because HERG current is sensitive to the extracellular potassium concentration, it has been thought that maintaining a "high" serum potassium value may promote shortening of action potential duration and the QT interval, and limited clinical trails have been performed confirming this. Drugs that increase potassium channel current, although normally not used clinically as antiarrhythmic agents, can experimentally shorten the action potential duration and suppress arrhythmias.

As described above, defective protein trafficking of mutant HERG channels is a common mechanism in LQT2. Our findings, described below in the Examples, demonstrate that the trafficking defect can be corrected and that the mutant channels can function to express increased amplitude HERG current by treatment with fexofenadine. These findings offer an approach to treating LQT2 mutations in patients.

The present invention is a method of shortening a prolonged QT interval and treating the resultant cardiac arrhythmia. In one embodiment, the method comprises treating a suitable patient with an effective amount of fexofenadine. A "suitable" patient is described below. An appropriate amount of fexofenadine is also discussed below.

Selection of Patients

Typically, a suitable patient will meet the following criteria:

Age range is infant to adult (no exclusion)

Specific genetic mutation is N470D or G601S or other HERG trafficking defective mutations. A HERG trafficking-defective mutation is defined as a mutation that generates only the immature protein band (135 kDa) on Western blot and not the mature protein band (155 kDa). Thus, it is easily recognized on Western blot by the absence of the larger band. This results from trapping of the immature protein in the endoplasmic reticulum with its failure to undergo maturation (e.g., complex or N-linked glycosylation) (Zhou, et al., supra, 1998).

Measurable QT interval

On an ECG, depolarization, of the ventricles is associated with the appearance of the QRS complex, while repolarization of the ventricles occurs with the T wave. Thus the "QT interval" is a measure of the time for the ventricle to depolarize and repolarize during each heart beat. The QT interval can easily be measured with an accuracy of about 10 milliseconds. In long QT syndrome, the QT interval becomes prolonged beyond normal and is associated with serious and life-threatening arrhythmia. Because the QT interval is sensitive to heart rate, the rate corrected QT interval (QTc, Bazett's equation) will also be measured.

Treatment Plan

The following is a preferred treatment plan: Patients will be admitted to hospital and placed on continuous telemetry. Baseline laboratory data (blood tests, ECG) will be obtained and reviewed before patients are enrolled. Two amps of $MgSO_4$ will be available in the room for the treatment of acute arrhythmias. Three control ECGs (recorded digitally at standard machine settings) will be recorded at 6 hour intervals.

On day two (at 6 a.m.) an i.v. will be started. Standard (PDR) oral fexofenadine dosing routines will be followed. Typically, the patient will first be given fexofenadine 60 m.g., p.o., q 12 hours.

On day three the drug dose will be changed to 180 m.g. q.d. During drug dosing (days two and three), an ECG will be obtained predose, at 1, 2, 3, 4, 6, 12 and 24 hours later. Patients will be discharged on day four, or late on day three if no effect on the ECG has occurred. A final ECG will be obtained in the outpatient setting 7 days later.

A second preferred option exists where patients get 60 mg b.i.d. for 3 days (allows drug to reach steady-state in blood) followed by 3 days of drug washout. (The washout period allows one to examine whether QT interval shortens when no drug is administered). The patient would then receive the higher dose protocol of 180 mg q.d. using a similar time protocol only if the lower dose protocol failed to lessen the QT interval.

Successful treatment at this point is a statistically significant shortening of the QT interval.

Preferably, blood for fexofenadine plasma levels will be drawn three hours after drug dosing on day three. Typically, blood samples will be frozen and analyzed only if needed. There are published data on blood levels achieved at various dosing schemes. These data potentially confirm the serum levels we achieve and correlate this with shortening of the QT interval.

If a patient responds suitably, the patient would take standard oral doses of fexofenadine.

One of skill in the art will envision other ways of treating a patient with a suitable amount of fexofenadine. The critical feature of the above-identified protocol is that an effective amount of fexofenadine be administered to this patient such that the desired treatment outcome is obtained.

Measurement of Effect

The objective definitions of a successful treatment include:

Change (reduction) in duration of the QT interval (post-pre)

Measurement of QT interval

QTc calculation (Bazetts formula, which corrects for changes in heart rate)

The goal of the present invention is to shorten the QT (also the QTc). This is beneficial, and correcting the interval to within normal limits is ideal. A normal QTc for men is less than approximately 440 msec and for women less than approximately 460 msec, although there is not absolute agreement on these numbers. A prolonged QT interval is considered a risk factor for arrhythmias and sudden death. Literature suggests that mortality with a congenital prolonged QT may approach 50% in untreated, symptomatic individuals (Schwartz and Locati, *Eur. Heart. J.* 6(Supp. D):103–114, 1985).

EXAMPLES

Example 1

Multiple Mechanisms for the Pharmacological Rescue of LQT2 Mutant Channels

Methods

Site-directed Mutagenesis and Transfection. The LQT2 mutations N470D (asparagine to aspartic acid), G601S (glycine to serine) and V822M (valine to methionine) have been shown previously to be trafficking-defective channel proteins. Zhou, et al., *J. Biol. Chem.* 274:31123–31126, 1999; Ficker, et al., *J. Biol. Chem.* 277:4989–4998, 2002; Furutani, et al., *Circulation* 99:2290–2294, 1999.

The HERG N470D, G601S and V822M mutations were generated by site-directed mutagenesis of wild-type HERG cDNA using the GeneEditor™ in vitro mutagenesis system (Promega). Transfection of human embryonic kidney (HEK293) cells with HERG wild-type, N470D, G601S and V822M cDNA was carried out with Lipofectamine™ (Invitrogen). Stable cell lines were generated through G418 (Invitrogen) antibiotic selection; successful transfection was confirmed by Western blot analysis and the cell lines were cultured in MEM, as previously described.

Patch-Clamp Recording Method. Whole cell recordings were performed using suction pipettes as described previously. Zhou, et al., *J. Biol. Chem.* 273:21061–21066, 1998; Zhou, et al., *Biophys. J.* 74:230–241,1998. Cells were superfused with Tyrode solution containing (mmol/L) 137 NaCk, 4 KCk, 1.8 $CaCl_2$, 1 $MgCl_2$, 10 glucose and 10 HEPES (pH 7.4 adjusted with NaOH). The bath solution was exchanged completely within two minutes. The internal pipette solution contained (mmol/L) 130 KCl, 1 $MgCl_2$, 5 EGTA, 5 MgATP, and 10 HEPES (pH 7.2 adjusted with KOH). An Axopatch 200B patch clamp amplifier was used to record membrane current. Computer software (pCLAMP8.2, Axon Instruments) was used to generate voltage clamp protocols, acquire data, and analyze current signals. Patch electrodes typically had resistances of 2–5 MΩ. Series resistance compensation was approximately 75%. Data were not leak corrected. HEK293 cells during depolarizing steps display a small amplitude endogenous current that is not present during the recording of tail current. Zhou, et al., supra, 1998. All patch clamp experiments were performed at 22–23° C. within 2 hours of removing cells from culture conditions.

Drugs and Experimental Protocols. Research grade terfenadine (471.7 mw) was obtained from Sigma Chemicals, Inc. Research grade fexofenadine HCl (538.1 mw) was obtained from Hoechst Marion Roussel, Inc. E-4031 was obtained from Eisai, Ltd (Ibaraki, Japan). Sodium-phenylbutyrate (4PBA) was obtained from Triple Crown USA, Inc.

Pharmacological rescue: Fexofenadine was dissolved in MEM to give stock solutions, and the final drug concentrations were made by further dilutions in MEM. Terfenadine and 4PBA were dissolved in absolute alcohol to give stock solutions, and the final drug concentrations were made by further dilutions in MEM (maximal alcohol concentration 0.01%). HEK293 cells expressing the N470D or G601S mutations were cultured at 37° C. in drug-containing MEM for 24 hours. Drugs were removed by culturing cells for one hour in drug-free MEM at 37° C. before whole cell recording.

Temperature-dependent rescue and drug block: Terfenadine or fexofenadine were dissolved in absolute alcohol to give stock solutions and the final drug concentrations were obtained by diluting the stock solution with Tyrode solution (maximal alcohol concentration 0.01%). To examine drug block of N470D channels, HEK293 cells expressing the mutation were cultured at 27° C. for 24 hours to induce temperature-dependent rescue of functional channels. January, et al., *J. Cardiovasc. Electrophysiol.* 11:1413–1418, 2000; Zhou, et al., *J. Biol. Chem.* 274:31123–31126,1999. E-4031 was dissolved as previously described. Zhou, et al., supra, 1998.

Curve Fitting and Statistical Methods. Data are given as mean±SEM, where n=number of cells. Voltage-dependence of activation was determined by fitting peak tail current with a Boltzmann equation ($y=1/[1+\exp(-(E-E_h)/k)]$), where E is membrane voltage, $E_h$ is the voltage at which 50% of channels are activated, and k is slope factor. Concentration-dependent effects were fit to the Hill equation ($I_{drug}/I_{control}=1/[1+(D/X_{50})^{nH}]$), where D is the drug concentration, $X_{50}$ is the drug concentration for 50% pharmacological rescue ($RC_{50}$) or 50% block ($IC_{50}$), and nH is the Hill coefficient. Student's t-test was used to calculate statistical significance and a P value of <0.05 was considered significant.

Results

Pharmacological Rescue of the N470D LQT2 Mutation and HERG Channel Block by Terfenadine.

Pharmacological rescue of the N470D mutation by terfenadine is shown in FIG. 1. The voltage clamp protocol, which was applied at 15 second intervals, is shown in FIG. 1A (upper trace). From a holding potential of −80 mV, 4 second long depolarizing steps were applied in 10 mV increments from −70 to 70 mV, followed by a 5.7 second long step to −50 mV to record tail current. The control data shows current recorded from a cell expressing the N470D mutation and cultured at 37° C. It displays a small amplitude endogenous current during the depolarizing step, and a very small amplitude HERG tail current following the repolarizing step to −50 mV (arrow). When the same cell line was cultured at 37° C. in 1 µM terfenadine for 24 hours, followed by drug-free culture conditions for one hour, HERG current was present (note large amplitude tail current). The I–V plots with activation curves fitted to the peak tail current amplitude are shown in FIG. 1B. For control conditions a very small amplitude HERG tail current was recorded (n=5). Culturing cells in 0.05 µM terfenadine resulted in no pharmacological rescue (n=7). In contrast, culturing cells in 1 µM terfenadine resulted in the pharmacological rescue of large amplitude HERG current (n=5).

However, 1 µM terfenadine blocks HERG channels. This is shown for wild-type HERG channels (FIG. 1C, n=4) and temperature-dependent rescued N470D channels (FIG. 1D, n=4). From a holding potential of −80 mV, cells were depolarized for 4 seconds to 20 mV followed by a 5.7 second long step to −50 mV to record tail current, and the protocol was repeated at 15 second intervals. In these experiments, peak tail current amplitude in each cell was normalized to a control value recorded one minute before drug exposure. Application of 1 µM terfenadine resulted in the complete block of HERG current in wild-type and temperature-dependent rescued N470D mutant cells (FIG. 1C and D). These data agree with previous reports of high affinity HERG channel block by terfenadine ($IC_{50}=56$ nM) Pratt, et al., *Clin. Exp. Allergy* 3:212–216, 1999a, which contributed to its withdrawal from the market because of acquired long QT syndrome.

Pharmacological Rescue of the N470D LQT2 Mutation by Fexofenadine

Figure 2:
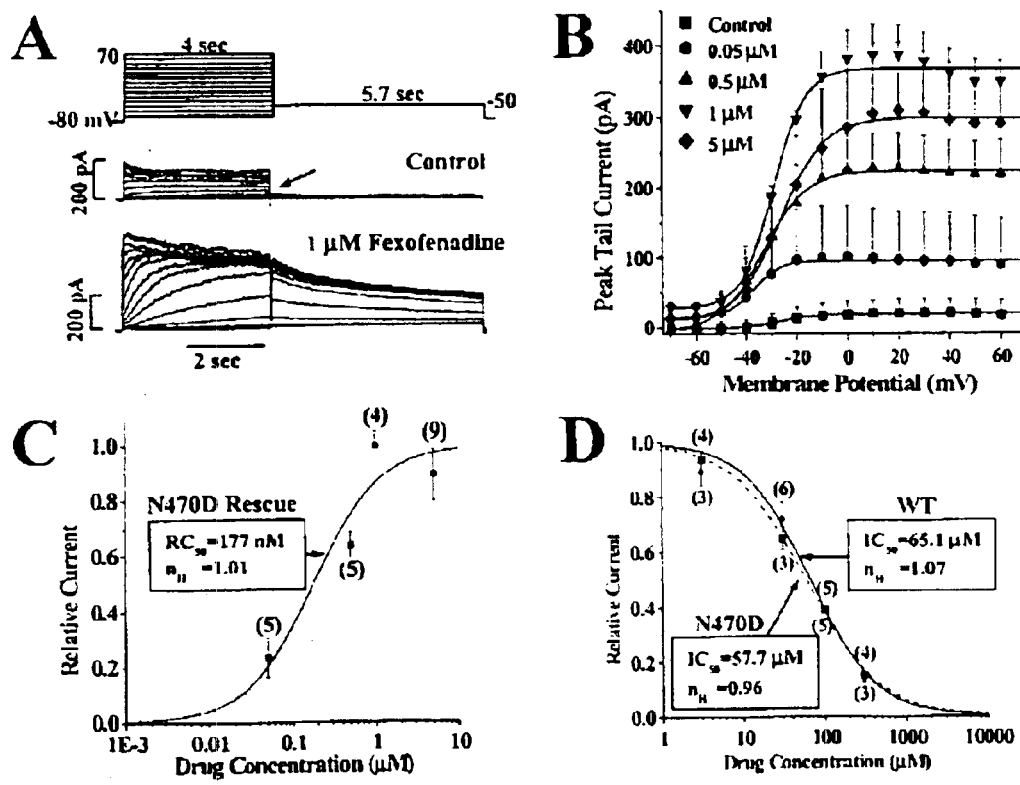
FIG. 2 shows the effect of fexofenadine on HERG wild-type (WT) and N470D mutant channels. FIG. A shows the voltage clamp protocol and representative current records for control conditions and after fexofenadine treatment.

Pharmacological rescue of the N470D mutation by fexofenadine is shown in FIG. 2. Current was elicited with the voltage clamp protocol shown in FIG. 2A (upper trace, same protocol as in FIG. 1A). The control record shows current recorded from a cell expressing the N470D mutation cultured at 37° C. A small amplitude endogenous current is present during depolarization along with a very small amplitude HERG current (note diminutive tail currents, arrow). Culturing the same cell line at 37° C. in 1 µM fexofenadine for 24 hours resulted in the emergence of HERG current (note large amplitude tail current), which was not increased further by culturing cells for 48 hours in drug. In contrast to terfenadine, fexofenadine rescued HERG current could be recorded without culturing cells in drug-free MEM before whole cell recording.

To confirm that the pharmacologically rescued current was carried by HERG channels, in some experiments the cells were exposed to E-4031 (100–300 nM) which completely blocked the fexofenadine rescued current (n=8 cells, protocol same as FIGS. 1C,D, data not shown). Plots of fexofenadine rescued peak tail current amplitude versus voltage, and the resulting Boltzmann fits, are shown in FIG. 2B (same protocol as used in FIG. 1B). N470D expressing cells were cultured for 24 hours in the presence of control conditions (no drug, n=5) or in 0.05 (n=5), 0.5 (n=5), 1.0 (n=5) or 5 µM (n=9) fexofenadine. A very small amplitude HERG current was present for control conditions, and fexofenadine resulted in concentration-dependent pharmacological rescue.

Quantitative analysis of the concentration-dependence of pharmacological rescue was performed by plotting peak tail current amplitude recorded at −50 mV following full activation at 20 mV as a function of the rescuing fexofenadine concentration. The resulting plot when fit with a Hill equation gave a $RC_{50}$ value of 177±6 nM and Hill coefficient of 1.01, consistent with high affinity rescue through a single drug binding site (FIG. 2C).

Fexofenadine is reported to only weakly block HERG wild-type channels and therefore may possibly rescue trafficking-defective HERG protein without blocking channel function. Therefore, we studied fexofenadine's ability to block HERG wild type and temperature-dependent rescued N470D channels (FIG. 2D). Tail currents were recorded using same protocol as in FIGS. 1C and 1D. Peak tail current amplitude at steady-state drug block in each cell was normalized to a control value recorded one minute before drug exposure. Averaged normalized peak tail current amplitude is plotted versus the fexofenadine concentration (3, 30, 100 and 300 $\mu$M), and these data were fit with the Hill equation. The $IC_{50}$ value for HERG wild-type channels was 65.1±8.3 $\mu$M with a Hill coefficient of 1.07, and for N470D channels was 57.7±2.8 $\mu$M with a Hill coefficient of 0.96. The $IC_{50}$ values were not different (p>0.05). The $IC_{50}$ values for fexofenadine block of HERG wild-type and N470D channels exceed the $RC_{50}$ value for pharmacological rescue of the N470D channel by 368- and 326-fold, respectively.

Pharmacological Rescue of the G601S LQT2 Mutation by Fexofenadine

Figure 3:
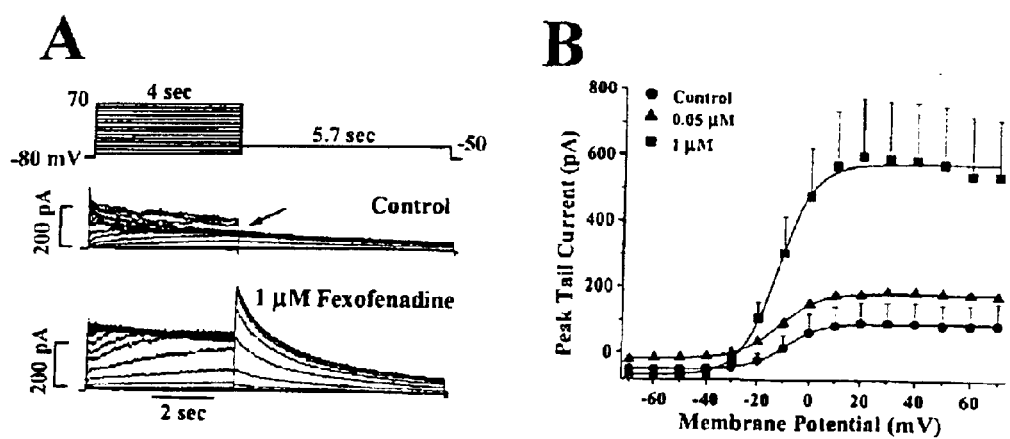
FIG. 3 shows the effect of fexofenadine on the HERG G601S mutation.

In order to test whether fexofenadine might rescue multiple HERG mutations at similar drug concentrations, we studied another trafficking-defective LQT2 mutation, G601S. Ficker, et al., *J. Biol. Chem.* 277:4989–4998, 2002; Furutani, et al., *Circulation* 99:2290–2294,1999. Fexofenadine mediated pharmacological rescue of the G601S mutation is shown in FIG. 3. The voltage clamp protocol and representative current records are shown in FIG. 3A (same protocol as that used in FIGS. 1A,B and 2A,B). The control record shows current recorded from HEK293 cells stably expressing the G601S mutation cultured at 37° C. The G601S expressing cells have a small amplitude HERG current (arrow) indicating that some mutant channels reach the plasma membrane. Ficker, et al., supra, 2002. Furutani, et al., supra, 1999. Culturing the same cell line in 1 $\mu$M fexofenadine at 37° C. for 24 hours resulted in the appearance of large amplitude HERG current. Similar to the N470D mutation, the HERG current could be recorded without culturing cells in drug-free MEM solution before whole cell recording, and the pharmacologically rescued current was blocked by E-4031 (100–300 nM, n=3, data not shown). The I–V relations for peak tail current amplitude for the G601S mutation are shown in FIG. 3B (same protocol as in FIGS. 1B and 2B). For these experiments, cells were cultured for 24 hours in control (no drug, n=4) conditions or in 0.05 (n=3) or 1.0 $\mu$M (n=6) fexofenadine. The results show a small amplitude HERG current for control conditions, and its concentration-dependent, pharmacological rescue with fexofenadine.

Lack of Pharmacological Rescue of the V822M LQT2 Mutation by Fexofenadine

Figure 4:
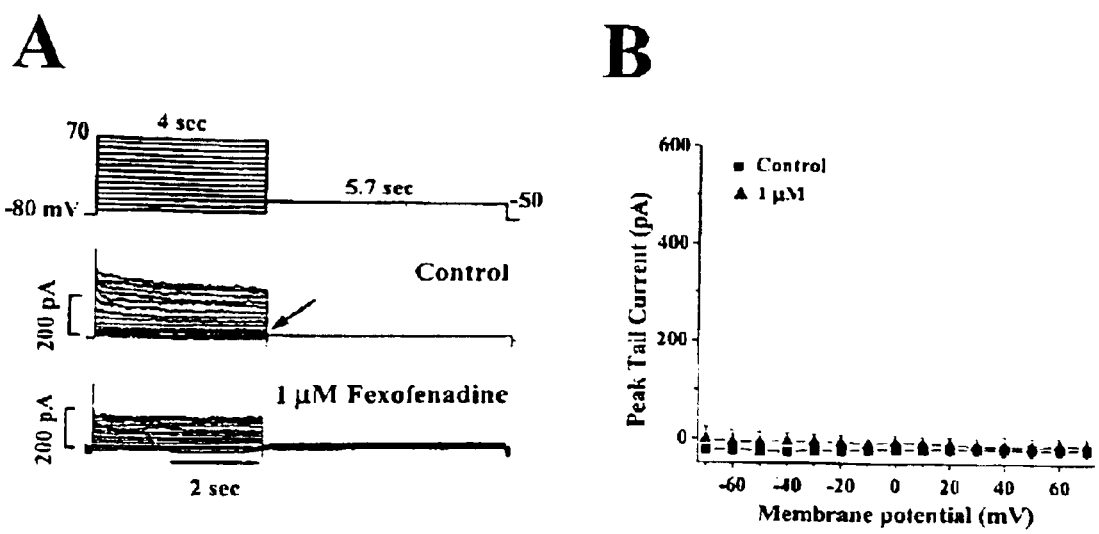
FIG. 4 shows the lack of pharmacological rescue of the HERG V822M mutation.

We studied a third LQT2 mutation, V822M, located in the C-terminus of the HERG channel in the nucleotide binding domain that we have previously confirmed to express the immature form of the protein that is trafficking-defective. The voltage clamp protocol and representative current records are shown in FIG. 4 (same protocol as that used in FIGS. 1A,B, 2A,B, 3A). The control record shows current recorded from HEK293 cells stably expressing the V822M mutation cultured at 37° C. A small amplitude endogenous current is present with the depolarizing steps, but unlike the N470D and G601S transfected cells there is no HERG current (arrow, n=4). Culturing in 1 $\mu$M fexofenadine at 37° C. for 24 hours resulted in no pharmacological rescue of HERG current (n=4), and this is shown in the I–V plots in FIG. 4B.

Discussion

These data are the first to show pharmacological rescue of human LQT2 mutations at drug concentrations that do not block HERG channels. Although fexofenadine and terfenadine rescued mutated HERG channels, only fexofenadine did so at drug concentrations that did not cause channel block. Our data show that the $RC_{50}$ value for rescue of the N470D mutant channel protein is ~350-fold less than the $IC_{50}$ values for block of HERG wild-type or N470D mutated channels. The concentration-response curve for pharmacological rescue (FIG. 2C) is below the concentration-response curves for channel block (FIG. 2D), and there is no overlap except for minimal block at the highest pharmacological rescue concentration.

Our data show that the half-maximal activation voltages ($V_{1/2}$) for the N470D mutation are shifted negatively compared to the values obtained for wild-type or G601S mutant channels (FIGS. 1B, 2B and 3B). This is in agreement with previously published data, and confirms that the pharmacologically rescued channels retain electrophysiological properties similar to channels expressed in oocytes and mammalian cells at reduced temperature. Zhou, et al., supra, 1999; Furutani, et al., supra, 1999; Sanguinetti, et al., *Proc. Natl. Acad. Sci. USA* 93:2208–2212, 1996. Thus, fexofenadine does not alter these biophysical properties of the pharmacologically rescued channels. Weak block by fexofenadine of HERG wild-type channels has been reported previously. Pratt, et al., *Clin. Exp. Allergy* 3:212–216, 1999a. Our data extend this observation to show that HERG wild-type and temperature-dependent rescued N470D mutant channels have similar low affinities for block by fexofenadine. Thus the N470D mutation, which is located in the S2 transmembrane spanning domain, does not alter drug affinity for the putative drug block domain located in the pore-S6 region of the HERG channel protein. Mitcheson, et al., *Proc. Natl. Acad. Sci. USA* 97:12329–12333, 2000; Lees-Miller, et al., *Circ. Res.* 86:507–513, 2000.

Defective protein trafficking is emerging as a common consequence of gene mutations. The molecular mechanisms underlying the intracellular retention of trafficking-defective proteins and the pharmacological rescue of trafficking-defective LQT2 channels are not well understood. Trafficking-defective proteins are thought to arise from mutations that cause improper protein folding or incorrect molecular assembly in the endoplasmic reticulum and/or Golgi apparatus, resulting in their retention and degradation by quality control machinery. Zhou, et al., *J. Biol. Chem.* 273:21061–21066, 1998; Rodgers, et al., *Eur. Respir. J.* 17:1314–1321, 2001; Smith, et al., *Pharmacol. Rev.* 50:493–514,1998.

Some compounds, such as 4PBA or glycerol, have been shown to improve trafficking of mutant proteins in disease models such as cystic fibrosis and nephrogenic diabetes insipidus, Tamarappoo, et al., *J. Clin. Invest.* 101:2257–2267, 1998; Loo, et al., *J. Biol. Chem.* 272:709–712,1997; Rubenstein, et al., *Am. J. Respir. Crit. Care Med.* 157:484–490, 1998, and are thought to act as protein stabilizing agents ("chemical chaperones"). These compounds frequently require very high concentrations (mM to M). We obtained similar findings with glycerol (~1M) in the N470D mutation, Zhou, et al., *J. Biol. Chem.* 274:31123–31126, 1999, whereas culture for 24 hours in 2.5–5.0 mM 4PBA, the concentration range required for rescue of the cystic fibrosis ▲F508 mutation, did not rescue N470D current (n=3, data not shown).

Our present findings provide new insight. Fexofenadine mediated pharmacological rescue had a $RC_{50}$ of 177 nM with a Hill coefficient of 1.01, suggesting a single high affinity drug binding site for rescue. Furthermore, high affinity HERG channel block is not a requirement for pharmacological rescue as this can occur without HERG channel block, thus rescue and block are not inextricably linked and these processes can be uncoupled. Taken together, these data suggest that the mechanism for fexofenadine mediated rescue may not involve drug binding within the pore-S6 drug binding domain that is postulated to mediate HERG channel block, or fexofenadine might bind to the pore-S6 drug binding domain but does so without impeding ion flow through the channel at the drug concentrations required for pharmacological rescue. A possibility is that multiple mechanisms may exist for pharmacological rescue of LQT2 mutations.

The N470D mutation is located within the S2 transmembrane spanning domain and the G601S mutation is located within the S5-pore extracellular linker of the HERG channel protein. Fexofenadine rescued both mutations demonstrating that a single pharmacological agent is capable of rescuing mutations in different regions of the channel. Fexofenadine did not, however, rescue the V822M mutation. Thus, while fexofenadine rescued multiple LQT2 mutations, it is not capable of rescuing all trafficking-defective LQT2 mutations, and this observation agrees with the recent report by Ficker and colleagues that high affinity HERG channel blocking drugs failed to rescue two other C-terminus mutations. Ficker, et al., supra, 2002. Our data also show that the N470D and G601S mutations, but not the V822M mutation, express very small amplitude HERG currents when cultured under control conditions, suggesting that small numbers of channels escape the quality control mechanism to insert into the plasma membrane. A possibility is that the presence of small amplitude HERG current recorded under control conditions could serve as a "signature" for LQT2 mutant channel proteins that might undergo successful pharmacological rescue. Our observations add importance to not only identifying gene mutations, but to elucidating their biological consequences and potential for rescue through functional expression.

These findings have the potential for therapeutic application. Fexofenadine is a FDA approved drug that is widely available by prescription as an antihistamine agent. It is thought to not affect the QT interval on the ECG even when administered in doses that exceed ten-fold recommendations, Pratt, et al., Am. J. Cardiol. 83:1451–1454, 1999b. Following the oral administration of 60 or 180 mg fexofenadine to healthy volunteers, the mean $C_{max}$ was 141 and 494 ng/mL or 262 and 918 nM, respectively, and protein binding of fexofenadine is reported to be 60–70%. Thus, serum concentrations achieved in patients are within the concentration range required for the pharmacological rescue of mutant LQT2 channels found in our experiments. Consequently, our results have the potential for therapeutic application and represent a new paradigm for antiarrhythmic drug therapy in some trafficking-defective LQT2 mutations.

Example 2

Pharmacoloqical Rescue of Human K$^+$ Channel LQT2 Mutations HERG Rescue without Block In the present work, we investigated the biochemical mechanism of pharmacological rescue of LQT2 mutations with fexofenadine. Our findings suggest that multiple mechanisms may underlie pharmacological and temperature-dependent rescue, and that under some conditions these rescue mechanisms may be additive.

Materials and Methods

Site-Directed Mutagenesis and Transfection

Wild-type (WT) HERG channels, the LQT2 mutations N470D and G601S, and the engineered mutations N598Q, S620T and N470D/S620T were studied. N470D and G601S have been shown to be trafficking-defective channel proteins (Zhou, et al., supra, 1998; Ficker, et al., supra, 2002; Rajamani, et al., supra, 2002; Furutani, et al., Circulation 99:2290–2294,1999). The N598Q mutation disrupts N-linked glycosylation (Gong, et al., Am. J. Physiol. 283:H77–84, 2002). The S620T mutation disrupts HERG channel inactivation and inhibits high affinity drug block (Herzberg, et al., J. Physiol. 511:3–14, 1998; Ficker, et al., Circ. Res. 82:386–395, 1998; Zhang, et al Circ. Res. 84:989–998, 1999).

The N470D, G601S, N598Q, S620T and N470D/S620T constructs were generated by site-directed mutagenesis of WT HERG cDNA using the GeneEditor in vitro mutagenesis system (Promega, Madison, Wis.). Stable transfection of human embryonic kidney (HEK293) cells with HERG WT, N470D, G601S, N598Q and N470D/S620T was carried out with Lipofectamine™ (Invitrogen, Carlsbad, Calif.). Cell lines were generated through G418 (Invitrogen, Carlsbad, Calif.) antibiotic selection, successful transfection was confirmed by Western blot analysis and the cell lines normally were cultured in MEM at 37° C., as previously described (Zhou, et al., supra, 1998).

Transient transfection of HEK293 cells with the S620T mutation was performed as previously described (Zhang, et al., supra, 1999). The HEK293 cell line we used has a small amplitude endogenous current that introduces minimal contaminating current (Mohammad, et al., Am. J. Physiol. 273:H2534–H2538, 1997; Zhou, et al., supra, 1998).

Patch-Clamp Recording Method

Membrane currents were recorded in the whole cell configuration using suction pipettes as described previously (Zhou Z., et al., supra, 1998; Rajamani, S., et al., supra, 2002). Cells were superfused with Tyrode solution containing (in mmol/L) 137 NaCl, 4 KCl, 1.8 CaCl$_2$, 1 MgCl$_2$, 10 glucose and 10 HEPES (normal pH 7.4 adjusted with NaOH). Solution exchange in the recording chamber was complete within 1 minute. The internal pipette solution contained (in mmol/L) 130 KCl, 1 MgCl$_2$, 5EGTA, 5 MgATP, and 10 HEPES (pH 7.2 adjusted with KOH). An Axopatch 200B patch clamp amplifier was used to record membrane current. Computer software (pCLAMP8.2, Axon Instruments, Union City, Calif.) was used to generate voltage clamp protocols, acquire data, and analyze current signals. Patch electrodes typically had resistances of 2–5 MΩ. Series resistance compensation was approximately 75–80% and data were not leak corrected. All patch clamp experiments were performed at 22–23° C. within 2 hours of removing cells from culture conditions.

Western Blot Analysis

The Western blot analysis procedure was previously described (Zhou, et al., supra, 1998; Ficker, et al., supra, 2002). In these experiments, whole cell lysates were subjected to SDS-polyacrylamide gel electrophoresis and then electrophoretically transferred onto nitrocellulose membranes. The nitrocellulose membranes were incubated with the HERG antiserum (1:20,000 dilution) at room temperature overnight, and the antibody was detected with an Ecl detection kit (Zhou, et al., supra, 1998). Each western blot shows data scanned from one nitrocellulose membrane and reproduced at constant grayscale intensity.

Drugs and Experimental Protocols. Research grade fexofenadine HCl was obtained from Hoechst Marion Roussel, Inc., and dissolved in MEM to give stock solutions from which final drug concentrations were made by further dilutions in MEM. Research grade terfenadine was obtained from Sigma Chemicals, Inc., and was dissolved in absolute alcohol to give stock solutions from which the final drug concentrations were made by further dilutions in MEM (maximal alcohol concentration 0.01%). E-4031 was a gift from Eisai, Ltd (Ibaraki, Japan) and was dissolved in water to give stock solutions, and the final drug concentrations were made by further dilutions in MEM.

Pharmacological Rescue: HEK293 cells expressing the mutations N470D, G601S or N470D/S620T were cultured at 37° C. for 24 hours in drug-containing solution to induce pharmacological rescue of functional channels, unless stated otherwise. After 24 hours, E-4031 was removed by culturing cells for one hour in drug-free MEM at 37° C. before whole cell recording, whereas, for fexofenadine drug washout was not required (Rajamani, et al., supra, 2002).

Temperature-dependent Rescue: HEK293 cells expressing the mutations N470D or N470D/S620T were cultured at 27° C. for 24 hours to induce temperature-dependent rescue of functional channels (January, et al., supra, 2000; Zhou, et al., supra, 1999; Rajamani, et al., supra, 2002).

Curve Fitting and Statistical Methods. Data are given as mean±SEM, where n=number of cells or Western blots. Statistical significance was tested using analysis of variance (ANOVA). A p value <0.05 was considered statistically significant. Concentration-dependent effects were fit to the Hill equation ($I_{drug}/I_{control}=1/[1+(D/X_{50})^{n_H}]$, where D is the drug concentration, $X_{50}$ is the drug concentration for 50% pharmacological rescue ($RC_{50}$) or 50% block ($IC_{50}$), and $n_H$ is the Hill coefficient.

Results

Western Blot Analysis of Pharmacological Rescue

HERG WT channel protein normally exists in two forms on Western blot analysis; a protein band of ~135 kDa representing the core-glycosylated, immature form of the channel protein in the ER, and a protein band of ~155 kDa representing the fully glycosylated (mainly N-linked), mature form of the channel protein transported to the plasma membrane (Zhou, et al., supra, 1998, Ficker, et al., supra, 2000; Gong, et al., supra, 2002; Zhou, et al., supra, 1998). A third protein band of ~132 kDa also can be shown under conditions where core-glycosylation is disrupted by enzymes (e.g., Endoglycosidase H, Zhou, et al., supra, 1998), drugs (tunicamycin, Gong, et al., supra, 2002) or engineered mutations in a N-linked glycosylation consensus site (N598Q, Gong, et al., supra, 2002).

LQT2 mutations that generate only the 135 kDa protein band are thought to represent trafficking-defective proteins that are retained in the ER and do not reach the plasma membrane to form functional channels (Zhou, et al, supra, 1998). When pharmacologically rescued with high affinity HERG channel blocking drugs such as E-4031, trafficking-defective LQT2 mutations show the appearance of the 155 kDa protein band along with increased HERG current. This suggested that the 155 kDa protein band is necessary for current generation, thus drugs causing pharmacological rescue were thought to restore normal protein processing of mutant channels.

Figure 5:
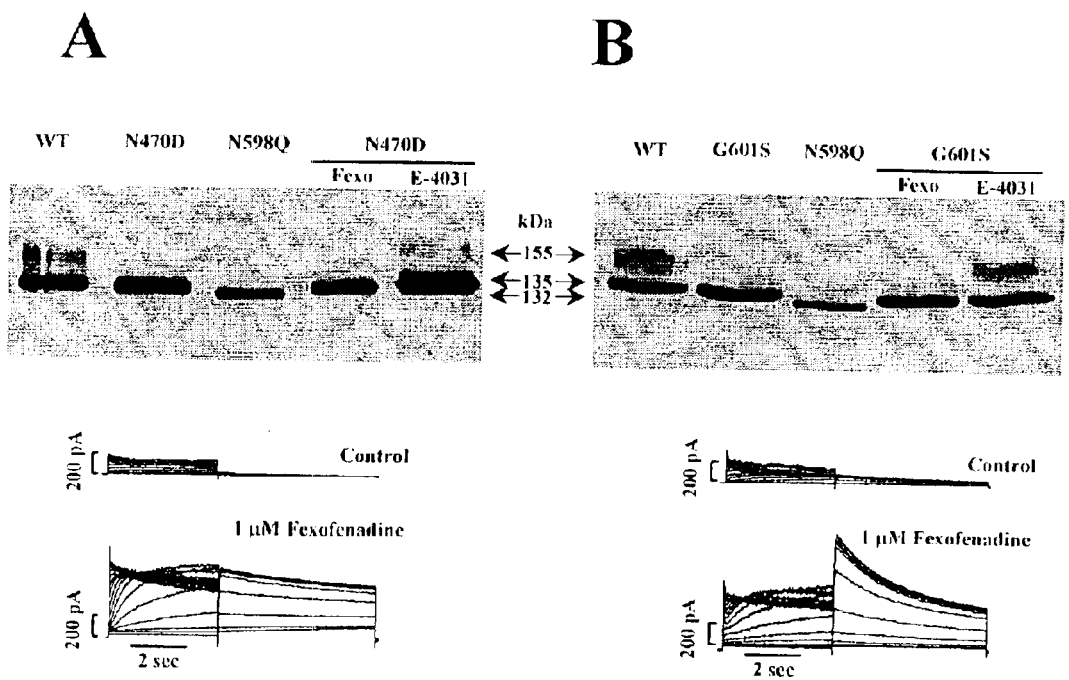
FIG. 5 is a Western blot analysis of HERG WT, the LQT2 mutations N470D and G601S, and the N-linked glycosylation consensus site mutation N598Q. Pharmacological rescue with fexofenadine, in contrast to E-4031, did not restore the 155 kDa protein band in N470D, (FIG. 5A) or G601S (FIG. 5B). Insets show HERG current recorded from N470D (FIG. 5A) and G601S (FIG. 5B) expressing cells for control conditions and following fexofenadine-mediated pharmacological rescue (voltage clamp protocol shown in FIG. 6). The tail current decay for N470D, compared to G601S, is slowed secondary to its negatively shifted gating properties.

FIG. 5 shows Western blot analyses of HERG WT, two LQT2 mutations, N470D (FIG. 5A) and G601S (FIG. 5B), and the N598Q mutation. In both panels, the WT lanes show two protein bands of 135 and 155 kDa. In contrast, for the N470D (FIG. 5A) and G601S (FIG. 5B) mutations a single protein band is present at 135 kDa, the expected finding for a trafficking-defective protein. The N598Q mutation in both panels shows a single protein band at 132 kDa, the expected finding when the Nlinked glycosylation consensus site is mutated. Despite the absence of both the 135 and 155 kDa protein bands, the N598Q mutation is capable of generating functional HERG channels (Gong, et al., supra, 2002, but see 18) suggesting that the presence of the glycosylated proteins (e.g., the 135 and 155 kDa bands) is not obligatory for the cell surface expression of HERG channels.

When cells expressing the N470D (FIG. 5A) or G601S (FIG. 5B) mutations were cultured in fexofenadine (1 μM) to cause the pharmacological rescue of HERG current (see inset traces below, see also Rajamani, et al, supra, 2002), the Western blot analyses surprisingly showed only the 135 kDa protein band. In contrast, when cells expressing the N470D (FIG. 5A) or G601S (FIG. 5B) mutations were cultured with E-4031 (5 μM), both the 135 and 155 kDa protein bands were present, which confirms previous findings (Zhou, et al., supra, 1999). Because the lack of the 155 kDa protein band with fexofenadine-mediated pharmacological rescue was unexpected, this pattern was confirmed in 21 Western blot analyses for the N470D mutation and in 10 Western blot analyses for the G601S mutation. Increasing the fexofenadine concentration to 5 or 100 μM did not result in the appearance of the 155 kDa protein band. In contrast, E-4031-mediated pharmacological rescue resulted in the presence of both the 135 and 155 kDa protein bands for the N470D (n=21 Western blots studied in parallel with fexofenadine) and G601S (n=10 Western blots studied in parallel with fexofenadine) mutations.

Figure 6:
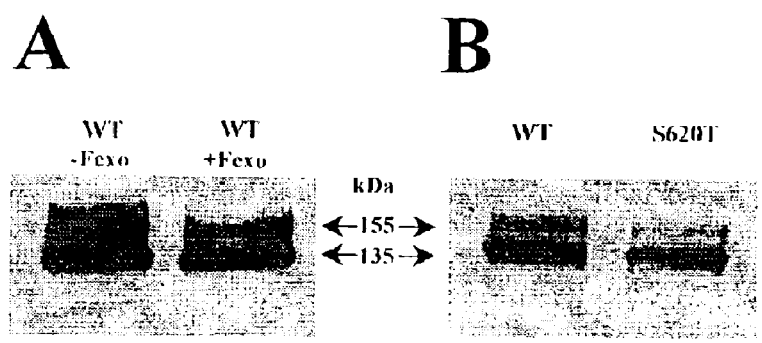
FIG. 6 is a Western blot analysis of HERG WT and S620T mutation.

In order to exclude that fexofenadine might directly inhibit N-linked glycosylation, we cultured the HERG WT cell line in fexofenadine (1 μM) for 24 or 48 hours, which had no effect on either the 135 or 155 kDa protein bands (FIG. 6A, n=3 Western blots).

The N470D/S620T Double Mutation: Temperature and Pharmacological Rescue

Drug block of HERG channels is mediated by drug binding to the pore-S6 region of the channel protein, and block is state-dependent and requires channel opening (Lees-Miller, et al., Mol. Pharmacol. 57:367–37420, 2000; Mitcheson, et al., Proc. Natl. Acad. Sci. USA 97:12329–12333, 2000; Chen, et al., Proc. Natl. Acad. Sci. USA 99:12461–12466, 2002). The S620T mutation, when expressed in Xenopus oocytes or HEK293 cells, disrupts inactivation to generate large amplitude current lacking a negative slope conductance, and drug block is markedly diminished (Herzberg, et al., supra, 1998; Ficker, et al., supra, 1998; Zhang, et al., supra, 1999). On Western blot analysis the S620T mutation generates both the 135 and 155 kDa protein bands (FIG. 6B, n=2 Western blots), the expected finding of a normally-trafficking channel.

Figure 7:
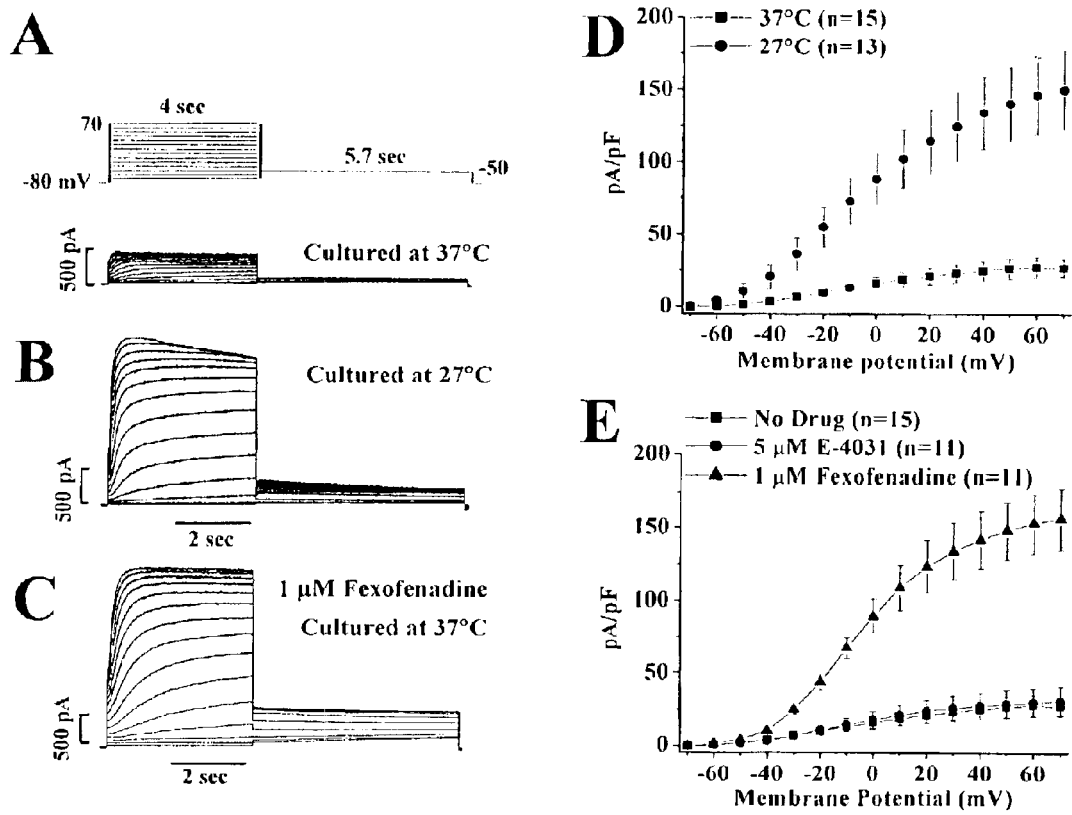
FIG. 7 illustrates HERG current and the N470D/S620T double mutation.

We tested whether incorporation of the S620T mutation into the N470D background would alter temperature or pharmacological rescue by E-4031 or fexofenadine. FIG. 7 shows results obtained with the N470D/S620T double mutation. FIG. 7A shows the voltage clamp protocol and representative currents recorded from a cell cultured at 37° C. These cells express a small amplitude HERG current with time- and voltage-dependent activation properties, and minimal inactivation properties, resulting from the S620T mutation (Herzberg, et al., supra, 1998; Ficker, et al., supra, 1998; Zhang, et al., supra, 1999) along with slowed tail current decay resulting from the negatively shifted gating properties of the N470D mutation (Sanguinetti, et al., supra, 1996; Zhou, et al., supra, 1999).

FIG. 7B shows the effect of culturing a cell expressing the N470D/S620T double mutation at 27° C. for 24 hours, which markedly increased HERG current amplitude. FIG. 7C shows the effect of culturing a cell in fexofenadine at 37° C. for 24 hours, which again markedly increased HERG current amplitude. Averaged data are shown in FIGS. 7D and 7E.

FIG. 7D shows I–V plots of HERG current measured at the end of the 4-second long depolarizing step for cells cultured at 37° C. or following temperature-dependent rescue at 27° C. for 24 hours. These data show that the N470D/S620T double mutation retains the property of temperature-dependent rescue, similar to the N470D mutation. The I–V plots lack a negative slope conductance at positive voltages, as expected from disruption of inactivation with the S620T mutation.

FIG. 7E shows I–V plots of HERG current following pharmacological rescue of the N470D/S620T double mutation by fexofenadine (1 μM) at 37° C. for 24 hours, which resulted in large amplitude HERG current. In contrast, cells cultured in E-4031 (5 μM) at 37° C. for 24 hours followed by a 1 hour drug-free washout period did not generate increased HERG current amplitude compared to control (no drug) conditions. These data demonstrate that fexofenadine-mediated pharmacological rescue was present, whereas, E-4031-mediated pharmacological rescue was abolished, with the inclusion of the S620T mutation to N470D. Astemizole (5 μM), another high affinity HERG channel blocking drug previously reported to cause pharmacological rescue of the N470D mutation, also did not produce pharmacological rescue of the N470D/S620T double mutation (n=6 cells, p>0.05 at all voltages).

Figure 8:
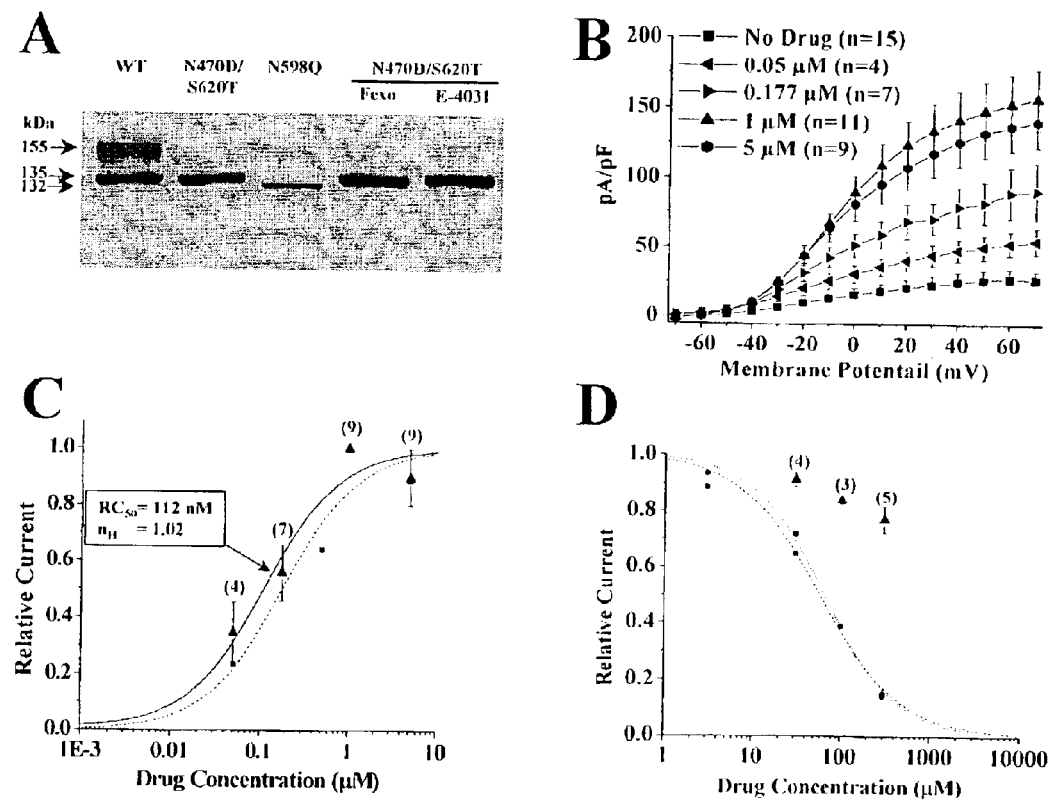
FIG. 8 illustrates concentration-dependence of pharmacological rescue and drug block of the N470D/S620T double mutation by fexofenadine.

FIG. 8A shows Western blot analysis of HERG WT, and the N470D/S620T and N598Q mutations. The HERG WT lane shows the expected two protein bands at 135 and 155 kDa. The N470D/S620T lane shows a single protein band at 135 kDa, suggesting that it is a core-glycosylated, poorly trafficking channel, and the N598Q lane shows a single protein band at 132 kDa, which lacks core-glycosylation. The final two lanes show the effect of the pharmacological rescue with fexofenadine and E-4031. Culturing cells expressing the N470D/S620T double mutation in 1 μM fexofenadine, which results in a 5-fold increase in HERG current (see FIG. 7E), shows only the 135 kDa band without the 155 kDa band (n=3 Western blots). Culture in E-4031, which fails to increase HERG current in the N470D/S620T double mutation, also showed only the 135 kDa protein band (n=3 Western blots). Thus, fexofenadine-mediated pharmacological rescue of the N470D mutation or the N470D/S620T double mutation, while increasing current amplitude, fails to cause the appearance of the 155 kDa protein band on Western blot.

We speculated that different drug binding domains might mediate pharmacological rescue and channel block by fexofenadine (Rajamani, et al., supra, 2002), and thus we used the N470D/S620T double mutation to test whether the inclusion of the S620T mutation would disrupt channel block, but not alter pharmacological rescue. N470D/S620T expressing cells were cultured for 24 hours at 37° C. in the presence of control conditions (no drug) or in 0.05, 0.177, 1.0 or 5.0 μM fexofenadine, similar to that previously done (see Rajamani, et al., supra, 2002). HERG current was measured at the end of the 4-second long depolarizing step (see FIG. 7A). I–V plots of averaged currents are shown in FIG. 8B. Compared to no drug treatment, fexofenadine treatment resulted in the concentration-dependent pharmacological rescue of N470D/S620T double mutation that was maximal at 1 to 5 μM. Quantitative analysis of the concentration-dependence of pharmacological rescue was performed by plotting normalized step current amplitude recorded at 70 mV as a function of the rescuing fexofenadine concentration.

The resulting plot is shown in FIG. 8C. When fit with the Hill equation it gave a $RC_{50}$ value of 112±42 nM and Hill coefficient of 1.02, consistent with high affinity pharmacological rescue through a single drug-binding site. These data are similar to that found previously with the N470D mutation pharmacologically rescued with fexofenadine, where the $RC_{50}$ was 179±6 nM with a Hill coefficient of 1.01 (Rajamani, et al., supra, 2002), and for comparison these data are included in FIG. 8C (dashed line). We conclude that the inclusion of the S620T mutation into the N470D background did not alter fexofenadine-mediated pharmacological rescue.

Fexofenadine weakly blocks HERG WT and N470D channels (Rajamani, et al., supra, 2002; Pratt, et al., Clin. Exp. Allergy 3:212–216,1999). We studied its ability to block temperature-dependent rescued N470D/S620T channels (FIG. 8D). From a holding potential of −80 mV, HERG current was activated with a single step to 70 mV for 4 seconds, followed by a step to −50 mV for 5.7 seconds, with the protocol applied every 15 seconds. After 10 minutes of drug exposure to each cell, peak current amplitude during the depolarizing step was normalized to the control value recorded one minute before drug exposure. The averaged normalized step current amplitude was plotted versus the fexofenadine concentration (30, 100 and 300 μM). FIG. 8D shows that fexofenadine produced minimal block of temperature-dependent rescued N470D/S620T channels. We previously showed that for temperature-dependent rescued N470D channels the $IC_{50}$ for block by fexofenadine was 57.7±2.8 μM with a Hill coefficient 0.96 and for WT channels the $IC_{50}$ was 65.1±8.3 μM with a Hill coefficient of 1.07 (see Rajamani, et al., supra, 2002), and for comparison these data are included in FIG. 8D (dashed lines). We conclude that the inclusion of the S620T mutation into the N470D background virtually abolished fexofenadine block of N470D/S620T channels.

Combinations of Temperature-Dependent and Pharmacological Rescue

Figure 9:
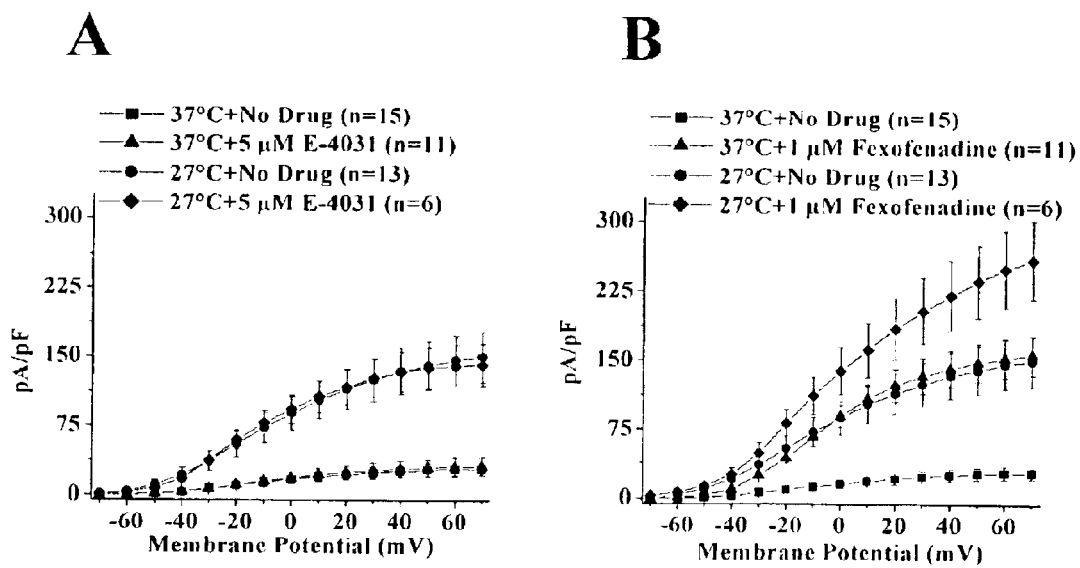
FIG. 9 graphs combination rescue.

We studied whether pharmacological rescue and temperature-dependent rescue were additive. To test for this, we cultured the cells at 37° C. or at 27° C. (to induce temperature-dependent rescue), and in the presence of E-4031 or fexofenadine for 24 hours. FIG. 9 shows I–V plots of averaged HERG currents measured at the end of the depolarizing step to voltages between −70 and 70 mV. FIG. 9A shows that culturing cells in E-4031 did not modify temperature-dependent rescue of HERG current. FIG. 9B shows that culturing the N470D/S620T expressing cells in fexofenadine for 24 hours resulted in an increase in HERG current amplitude at both culture temperatures, with the largest amplitude currents recorded following culture at 27° C. in the presence of fexofenadine. These data show that fexofenadine-mediated pharmacological rescue is additive to temperature-dependent rescue under conditions where E-4031-mediated rescue does not occur.

I claim:

1. A method of shortening prolonged QT intervals in a patient with a trafficking defective HERG mutation, wherein the patient has a prolonged QT interval comprising the step of treating the patient with an effective amount of fexofenadine, whereby the patient's prolonged QT interval is shortened and wherein the patient has a N47OD or G601S mutation.

2. The method of claim 1 wherein the fexofenadine is taken orally.

3. The method of claim 1 wherein the amount of fexofenadine is between 40–80 mg every 12 hours.

4. The method of claim 1 wherein the amount of fexofenadine is between 100–250 mg daily.

5. The method of claim 1 wherein the patient is monitored via an ECG.

6. The method of claim 1 additionally comprising the step of evaluating the patient's fexofenadine plasma levels after fexofenadine has been administered to the patient.

* * * * *